US012758322B2

(12) United States Patent
Balicki

(10) Patent No.: US 12,758,322 B2
(45) Date of Patent: Oct. 13, 2026

(54) CONTROL OF A ENDOVASCULAR ROBOTIC INSTRUMENT

(71) Applicant: KONINKLIJKE PHILIPS N.V., Eindhoven (NL)

(72) Inventor: Marcin Arkadiusz Balicki, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 19 days.

(21) Appl. No.: 18/710,959

(22) PCT Filed: Nov. 18, 2022

(86) PCT No.: PCT/EP2022/082468
§ 371 (c)(1),
(2) Date: May 16, 2024

(87) PCT Pub. No.: WO2023/089125
PCT Pub. Date: May 25, 2023

(65) Prior Publication Data

US 2025/0009450 A1 Jan. 9, 2025

Related U.S. Application Data

(60) Provisional application No. 63/281,207, filed on Nov. 19, 2021.

(30) Foreign Application Priority Data

Feb. 2, 2022 (EP) .................................... 22154694

(51) Int. Cl.
*A61B 34/32* (2016.01)
*A61B 34/00* (2016.01)
(Continued)

(52) U.S. Cl.
CPC .............. *A61B 34/20* (2016.02); *A61B 34/25* (2016.02); *A61B 34/32* (2016.02); *G06T 7/70* (2017.01);
(Continued)

(58) Field of Classification Search
CPC ......... A61B 34/20; A61B 34/25; A61B 34/32; A61B 2034/2065; A61B 2034/2074;
(Continued)

(56) References Cited

U.S. PATENT DOCUMENTS

2014/0276392 A1 9/2014 Wong et al.
2017/0050000 A1 2/2017 Randall
(Continued)

OTHER PUBLICATIONS

International Search report and Written Opinion of PCT/EP2022/082468, dated Mar. 16, 2023.

*Primary Examiner* — Bao Long T Nguyen

(57) ABSTRACT

A control device (100) for controlling movement of a medical instrument is presented. The control device comprises a limiting indicator providing unit (101) configured to provide an indicator (12) of a limiting position for an instrument (10) beyond which the position of the instrument is considered as out-of-limit, and a position providing unit (102) configured to provide a position (11) of the instrument from a received image including a portion of the instrument and/or retrieved movement of the instrument. The control device further comprises a controller (103) configured to control a movement of the instrument based on the indicator of the limiting position and the position of the instrument such that the position of the instrument maintains a predetermined relation with respect to the limiting position. This allows for an improved movement control for medical and other instruments.

17 Claims, 5 Drawing Sheets

(51) Int. Cl.

| | |
|---|---|
| ***A61B 34/20*** | (2016.01) |
| ***G06T 7/70*** | (2017.01) |
| *A61B 34/30* | (2016.01) |

(52) U.S. Cl.
CPC ................. *A61B 2034/2065* (2016.02); *A61B 2034/2074* (2016.02); *A61B 2034/301* (2016.02); *A61B 2034/303* (2016.02); *G06T 2207/10064* (2013.01); *G06T 2207/10068* (2013.01); *G06T 2207/30101* (2013.01)

(58) Field of Classification Search
CPC ........ A61B 2034/301; A61B 2034/303; A61B 5/489; A61B 2034/102; A61B 2034/252; A61B 2090/3612; A61B 2090/376; A61B 2090/3966; A61B 34/30; A61B 2090/0811; G06T 7/70; G06T 2207/10064; G06T 2207/10068; G06T 2207/30101; G06T 7/73; G06T 2207/10116; G06T 2207/30021; B25J 9/1676; B25J 9/1666
See application file for complete search history.

(56) References Cited

U.S. PATENT DOCUMENTS

| | | | | |
|---|---|---|---|---|
| 2017/0151027 | A1* | 6/2017 | Walker .................. | A61B 34/37 |
| 2020/0046434 | A1 | 2/2020 | Graetzel et al. | |
| 2020/0253670 | A1 | 8/2020 | Doisneau et al. | |
| 2021/0093406 | A1 | 4/2021 | Blacker et al. | |

* cited by examiner

CONTROL OF A ENDOVASCULAR ROBOTIC INSTRUMENT

CROSS-REFERENCE TO PRIOR APPLICATIONS

This application is the U.S. National Phase application under 35 U.S.C. § 371 of International Application No. PCT/EP2022/082468, filed on Nov. 18, 2022, which claims the benefit of European Patent Application No. 22154694.8, filed on Feb. 2, 2022, and U.S. Provisional Application Ser. No. 63/281,207, filed on Nov. 19, 2021. These applications are hereby incorporated by reference herein.

FIELD OF THE INVENTION

The invention relates to a control device, a method and a computer program for controlling movement of a medical instrument, as well as to an apparatus, a method and a computer program for moving a medical instrument.

BACKGROUND OF THE INVENTION

Navigating a medical instrument during or in preparation of a medical intervention can be a challenging and time-consuming task. The complexity of this task is yet increased by the fact that, after having navigated the medical instrument into a desired target position, accidental circumstances can cause the medical instrument to be dislodged out of the desired target position, thereby necessitating a time-consuming re-navigation of the medical instrument. In fact, an insufficient movement control over a medical instrument may not only necessitate additional navigational measures and hence an increase in an overall interventional duration, but may also lead to other medical complications, which can be harmful for a patient. There is therefore a need for an improved movement control for medical instruments.

SUMMARY OF THE INVENTION

It is an object of the invention to allow for an improved movement control for a medical instrument.

In a first aspect, the invention relates to a control device for controlling movement of a medical instrument, wherein the control device comprises a non-transitory memory that stores instructions and a processor that executes the instructions, wherein, when executed by the processor, the instructions cause the control device to:

- provide an indicator of a limiting position for an instrument beyond which the position of the instrument is considered as out-of-limit,
- provide a position of the instrument from a received image including a portion of the instrument and/or retrieved movement of the instrument,
- control a movement of the instrument based on the indicator of the limiting position and the position of the instrument such that the position of the instrument maintains a predetermined relation with respect to the limiting position.

The above-mentioned "instructions" may be defined or depicted as or implemented by "units" or "controller", as used in the next sections of these documents.

For example:

- a "limiting indicator providing unit" is configured (then) to provide said indicator of a limiting position for an instrument. Beyond the limiting position, the position of the instrument is preferably considered as out-of-limit
- a "position providing unit" is configured (then) to provide said position of the instrument from a received image including a portion of the instrument and/or retrieved movement of the instrument
- a "controller" is configured (then) to control said movement of the instrument based on the indicator of the limiting position and the position of the instrument such that the position of the instrument maintains a predetermined relation with respect to the limiting position.

Since an indicator of a limiting position for an instrument and furthermore a position of the instrument is provided, wherein the position of the instrument is provided from a received image including a portion of the instrument and/or retrieved movement of the instrument and wherein, beyond the limiting position, the position of the instrument is preferably considered as out-of-limit, information about the instrument's position in relation to its limits is accessible. Since a movement of the instrument is controlled based on the indicator of the limiting position and the position of the instrument such that the position of the instrument maintains a predetermined relation with respect to the limiting position, undesired motions of the instrument can be limited. The control device therefore allows for an improved movement control for the medical instrument.

The limiting indicator providing unit can be configured to (or corresponding instructions can further cause the control device to) determine the indicator of the limiting position itself and provide the determined indicator, or to receive the indicator from a corresponding determining unit or instructions or processor or a user interface and provide it for further processing. In addition or alternatively, the limiting indicator providing unit is optionally configured to (or corresponding instructions optionally cause the control device to) provide a representation of the indicator in the image so as to graphically represent the limiting position. The image may be the image from which the position of the instrument is provided. The representation of the indicator in the image may or may not be determined based on a user input. If determined based on a user input, the user input may particularly indicate an image position at which the representation of the indicator is to be placed.

The position providing unit is preferably configured to (or corresponding instructions preferably cause the control device to) determine the position of the instrument itself based on the image including the portion of the instrument and/or the retrieved movement of the instrument, and to provide the determined position. For determining the position of the instrument based on an image, the position providing unit may be configured to (or corresponding instructions may cause the control device to) apply image segmentation. Known image segmentation tools may be used, for instance, including U-Net convolutional neural network models.

The instrument for which the indicator of the limiting position is provided can be an instrument upon which motion is induced. In that case, the indicator could also be referred to as an induced motion limiting indicator, since it may indicate, via the limiting position, a limit for the motion induced upon the instrument. An induced motion could particularly refer to an accidental or unintended motion, i.e. a motion which is not in line with a movement corresponding to or expectable based on movement control signals of the controller. The induced motion can refer to an induced motion of the instrument with respect to a static environment or reference system, which could be referred to as an absolute induced motion. More generally, the induced motion can also refer to a relative motion, in which case it may be measured relative to an environment or reference system that moves itself. For instance, the induced motion may be measured relative to a potentially moving anatomical structure, like a vessel structure in a living patient. Changes in a relation between the position of the instrument and the limiting position may then arise, for instance, from a) movements of an anatomical structure relative to which the limiting position is fixed, if the instrument is moved differently or held at a fixed absolute position, b) motions induced upon the instrument by movements of the anatomical structure, if the limiting position is a fixed absolute position, and/or c) motions induced upon the instrument by movements of other instruments interacting with it.

In the introductory example in which a medical instrument has been navigated into a desired target position, the limiting position, i.e. the limiting position for the medical instrument indicated by the limiting indicator, could particularly correspond to the desired target position. The desired target position may, for instance, be determined by a user input or correspond to a last known position, such as a last known position after the user induced control of the instrument. The limiting position could correspond to the desired target position itself, i.e. be exactly or approximately equal to it. However, the limiting position could also correspond to the desired target position only up to a predefined tolerance. Motions induced upon the medical instrument may then be tolerated as long as they do not dislodge the medical instrument out of the target position to such a degree that the position of the medical instrument deviates from the desired target position beyond the tolerance. On the other hand, already an initial navigation of the medical instrument may be executed such that the medical instrument does not end up in the desired target position itself, but instead in a position corresponding to the desired target position only up to some safety margin, wherein the safety margin may already anticipate potential induced motions of the medical instrument. In this latter case, the limiting position indicated by the limiting indicator may again correspond exactly or approximately to the desired target position. This example goes to show that the predetermined relation of the position of the instrument with respect to the limiting position is to be understood broadly, particularly including both cases where the instrument is to be held in a fixed position and cases where the instrument may move as long as a predetermined condition on its relative position with respect to the limiting position is met. In this sense, through the limiting indicator, a tolerance for induced motions, and possibly all movements, of the instrument becomes quantifiable. Accordingly, the indicated limiting position could, in an embodiment, be understood as implying, or defining, a limit for induced motions of the instrument. However, the limiting position and its indicator may be defined independently of any motion being induced upon the instrument. More generally, for instance, the indicated limiting position could be understood as implying, or defining, a limit for all movements of the instrument.

The position of the instrument may refer to a location and/or an orientation of the instrument. In particular, the position of the instrument may refer to a location and/or an orientation of a predefined part of the instrument. However, the position of the instrument may also refer to a location and/or an orientation of a plurality of parts of the instrument, or be determined based thereupon, such as by averaging. The position of the instrument can be determined based on at least one of a) a received image including a portion of the instrument and b) retrieved movement of the instrument. Hence, for instance, the position of the instrument can be determined based on an analysis of an image showing the instrument, particularly based on predefined image features thereof. As mentioned above, known segmentation techniques may be used for this purpose. Additionally or alternatively to an image-based instrument positioning, a retrieved movement of the instrument may be used to determine the position of the instrument. A retrieved movement of the instrument may refer to movement control information recovered from previous movement control signals issued by the controller and/or to current control or movement parameters indicative of a position of the instrument. Said retrieved movement, previous movements or current movements, are preferably retrieved from information measured or collected from a tool, a robot and/or a motor which drives the motion of the instrument. This is preferable with respect to a tracking sensing system which usually implies embedding sensors in the instrument. It shall be understood that the position of the instrument provided by the position providing unit (or by the corresponding instructions causing the control device to provide this position) as a basis for the control by the controller is preferably a current position of the instrument.

As already indicated above, the indicator of the limiting position of the instrument, and hence implicitly also the limiting position itself, may be determined based on a user input, for instance. The indicator can also indicate a plurality of limiting positions, such as a limiting region. If for instance, the position of the instrument is determined based on an image of the instrument, the limiting position or region may be indicated with respect to the image. Movement control over the instrument may then be based on the image.

Depending on the type of indicator used and how the position of the instrument is determined, a type of input received by the controller for controlling the movement of the instrument may vary. Also the output of the controller may vary in type, particularly in accordance with the type of input received by the controller.

Preferably, the position of the instrument and the limiting position refer to positions in two or three spatial dimensions. At least the position of the instrument will typically move over time. The position providing unit may therefore be configured to (or corresponding instructions may cause the control device to) track the instrument's position, i.e. its movement, in time. While tracking the instrument's movement, the controller may be configured to check repeatedly, particularly continuously, whether the position of the instrument still satisfies the predetermined relation with respect to the limiting position. As already indicated above, this check may be carried out with a tolerance. That is to say, the controller may be configured to control the movement of the instrument such that the instrument maintains the predetermined relation with respect to the limiting position up to a tolerance. For instance, it may be tolerated and therefore not cause any control signals indicative of countermeasures, if the position of the instrument is determined to be beyond the indicated limiting position by less than a predefined tolerated distance. The controller may also take into account a tolerance in time for determining the control signals. A tolerance in time may indicate, for instance, that it is tolerated and therefore not causing any control signals indicative of countermeasures if the position of the instrument has been determined to be beyond the indicated limiting position for less than a predefined tolerated time period. The tolerated time period can be predefined to correspond to an integer number of N seconds, for example.

The control of the instrument's movement by the controller may refer to the controller providing control signals according to which the instrument can be physically moved. The control signals would then preferably comprise movement instructions regarding the position of the instrument, possibly provided continuously or repeatedly in time. The physical movement of the instrument, which can be based on the control signals provided by the controller, may be effected by a drive, for instance. In other embodiments, the controller could comprise physical moving means like a drive, in which case the controller would be configured to physically move the instrument itself. It should be noted that, while the control signals will preferably refer to the position of the instrument, wherein the position of the instrument may refer to a location and/or an orientation of the instrument in two or three spatial dimensions and additionally in time, the degrees of freedom of the instrument that are controllable by the controller may be limited. For instance, the controller may be configured to control only a single translational and a single rotational degree of freedom of the instrument, such as a translation of the instrument along a longitudinal axis of the instrument and its rotation about this axis.

Irrespective of the type of input and/or output of the controller, the controller is configured to control the movement of the instrument such that the position of the instrument maintains a predetermined relation with respect to the limiting position. The predetermined relation refers to a relation between the position of the instrument and the limiting position, i.e. the limiting position for the instrument. The predetermined relation may, as already indicated above, be viewed as a condition to be satisfied by the position of the instrument for a given limiting position. From this condition and the position of the instrument, the controller may be configured to determine how the instrument should, or is allowed to, be moved in order to make sure that the condition stays satisfied. The predetermined relation may be mathematically representable in terms of an inequality involving the position of the instrument and its limiting position, or respective indicators like an image or retrieved movement feature associated with the instrument and a corresponding limiting value defined by the indicator of the limiting position. For instance, the predetermined relation may mathematically correspond to the condition that a distance between a certain part of a medical instrument and a certain anatomical position should not decrease below a predefined threshold. However, controlling a movement of the instrument such that the predetermined relation is maintained by the instrument's position with respect to the limiting position does not necessarily require the control to be position-based, particularly not that the control is purely position-based. Additionally or alternatively, the controller may, for instance, control the instrument based on a signal or other control quantity that is indicative of a velocity of the instrument or a force on the instrument, possibly at the position provided for it. Limiting values may be defined also for such other control quantities, and these limiting values may translate, or correspond to, a certain limiting position. Satisfying a certain position-based condition may imply that a corresponding condition based on other control quantities like velocity or force is fulfilled and vice versa. Hence, a control "such that the position of the instrument maintains a predetermined relation with respect to the limiting position" includes control mechanisms that are not position-based. In this sense, a position of an instrument, as referred to herein, could be understood as referring not necessarily to a spatial position of the instrument, but possibly to a position in a space of other control quantities, like velocities or forces, for instance. A space of control quantities could also be understood as a configuration space, i.e. a space of configurations of the respective instrument.

It is understood that the predetermined relation to be maintained, or a corresponding condition, may be "activated" only over a predetermined time window, possibly starting after navigation of the medical instrument has been, or has been allegedly, completed. Outside of this time window, it may be acceptable that the condition corresponding to the predetermined relation is not satisfied. For instance, the medical instrument may be navigated past a critical anatomical point first, but thereafter induced motions of the medical instrument should not lead to the medical instrument approaching this critical anatomical point again.

An induced motion of the instrument could be understood as a passive movement caused by an active movement of another object or by an environment in which the instrument is positioned. For instance, motion may be induced upon the instrument by a patient undergoing a medical procedure carried out with the instrument, or by a further instrument used in combination with the instrument upon which the motion is induced. The induced motion of the instrument does not exclude an active movement of the instrument. In contrast, the instrument can itself also be moved, i.e. actively be moved, while at the same time being subject to the induced motion. In other words, active and passive movements of the medical instrument can be superimposed. In particular, the instrument may be actively moved so as to balance a passive movement like the induced motion. Yet more particularly, one may summarize: An active movement of the instrument may be such that it compensates for passive movements causing the position of the instrument to not maintain the predetermined relation with respect to the limiting position. It may be the active movements of the instrument that are the subject of control signal provided by the controller. Instead of effecting an active movement compensating for an induced motion corresponding to a passive movement of the instrument, the controller may also be configured to inhibit or even block the induced motion.

As just indicated, if a medical instrument is inserted in a patient's body during a medical procedure, any body movements of the patient may affect a position of the medical instrument relative to the body, such as relative to a particular anatomical landmark. The controller may therefore be configured, for instance, to control a movement of the medical instrument such that the medical instrument follows the body movements, at least to some extent. As also just indicated, however, another cause of induced motions of an instrument, particularly a medical instrument used for a medical procedure, can be a further instrument. In an embodiment, therefore, the above instrument is a first of two instruments, wherein the second of the two instruments may induce a motion upon the first instrument, i.e., when the second instrument is moved. The second instrument may particularly induce the motion upon the first instrument by its own movement. In other words, the induced motion of the first instrument can particularly be induced by a movement of the second instrument. This may particularly be the case if the first instrument and the second instrument are both medical instruments inserted in a patient's body.

In the presence of two instruments, the instrument upon which motion is induced will subsequently also be referred to as a first instrument, and the instrument inducing the motion upon the first instrument will subsequently also be referred to as a second instrument. Correspondingly, the position of the first instrument will subsequently also be referred to as a first position, and the position of the second instrument will subsequently also be referred to as a second position.

These instructions of the control device may further cause the control device to:

- provide a target indicator, the target indicator being indicative of a target position for the second instrument to be moved, and
- provide a second position, the second position being a position of the second instrument.

The above-mentioned "instructions" may be defined or depicted as or implemented by a "unit" or "controller", as used in the next sections of these documents.

For example:

- a "target indicator providing unit" is configured (then) to provide said target indicator, the target indicator being indicative of a target position for the second instrument to be moved, and
- a "second position providing unit" configured (then) to provide said second position, the second position being a position of the second instrument. The controller may be configured to control a movement of the second instrument based on the target indicator and the second position such that the second position approaches the target position.

Hence, said controller may primarily (or instructions may primarily further cause the control device to) control a movement of the second instrument, wherein, since this movement of the second instrument may accidentally induce a motion upon the first instrument, said controller may secondarily also (or instructions may also secondarily further cause the control device to) control a movement of the first instrument, namely to partially or fully compensate for, or inhibit or block, the induced motion.

The target indicator can be of the same type as the indicator of the limiting position of the first instrument. That is to say, the target indicator could correspond to the indicator of the limiting position of the first instrument, with the difference being that it indicates a target position for the second instrument instead of a limiting position for the first instrument. In an image of the two instruments, for instance, the two indicators could be represented in the same manner, just at different image locations and possibly in different orientations.

Similarly, the second position may be determined like the first position, just for the second instead of the first instrument. In particular, it shall be understood that also the position of the instrument is preferably a current position of the instrument, possibly determined based on an image analysis or based on a retrieved movement of the second instrument.

The controller may be configured to control a movement of the second instrument based on a user input, such as a user input received via a user interface, for instance. Apart from relying on such a user input, the controller may be configured to control the movement of the second instrument automatically. In more advanced embodiments, it would also be possible that a fully automatic control of the movement of the second instrument is implemented, i.e. without any user input. Conversely, it may in principle also be possible that the second instrument is primarily moved by a user, i.e. manually. In an exemplary embodiment, the instrument whose movement is controlled by the controller is a first of two instruments, wherein the second of the two instruments is manually driven and may induce a motion upon the first instrument, the control device allowing thus the first instrument to automatically maintain said predetermined relation with respect to the limiting position while the second instrument is manually driven. The controller may in that case be configured to provide a haptic feedback to the user. For instance, the controller may be configured to not allow the user to move the second instrument beyond the target position and/or to support any movement of the second instrument by the user that causes the second instrument to approach the target position. The user could be "not allowed" to move the second instrument beyond the target position due to the controller controlling the second instrument to push back. In fact, also in the semi-automatic embodiment, in which the user provides a user input based on which the controller controls the movement of the second instrument, the user may be "not allowed" to move the second instrument beyond the target position. In that case, "not allowed" may refer to the controller ignoring a respective user input.

Hence, additionally or alternatively to a) the controller being configured to control the movement of the second instrument based on the target indicator and the second position such that the second position approaches the target position, the controller may be configured to b) trigger an alert for the user when the second instrument approaches the target position beyond an alert limit, c) control a movement of the second instrument based on the target indicator and the second position such that the movement of the second instrument slows down when the second position is beyond an approach limit, and/or d) control a counteracting force applied to the second instrument or to a tool driving the second instrument, such a force being opposite to a manual force exerted by a user who would manually drive the second instrument, such counteracting force being exerted when the second position is beyond an approach limit, wherein optionally the approach limit is the target position and the counteracting force is sufficiently high to prevent the user to manually drive the second instrument beyond the target position, wherein further optionally the counteracting force gradually increases between the approach limit and the target position.

It may be preferred that the controller is configured to control the movement of the first instrument based further on the movement of the second instrument, such as based on a velocity with which the second instruments moves. This can allow for a better compensation for induced or other undesired motions. Moreover, the controller may be configured to restrict the movement of the first and/or the second instrument to predefined degrees of freedom. This can simplify the control. Also the complexity in a possibly needed user input can be decreased in this way. In an example, movements of the first and/or second instrument may be limited to translational motions, i.e. rotational motions may be excluded. Rotational motions have been observed to induce more complex motions on other instruments, such that excluding them can lead to an easier movement control.

A target indicator may also be provided for the first instrument. In fact, the indicator of the limiting position provided for the first instrument can itself at least temporarily also function as a target indicator for the first instrument. For instance, the controller may be configured to initially control the first instrument such that it approaches, or extends beyond, an indicated target position and subsequently such that it maintains a predetermined relation, such as, e.g., a maximum distance, with respect to the target position, particularly despite potential motions being induced upon it. In such a scenario, the target indicator would turn into an indicator of a limiting position over time.

Any of the two instruments may refer to a flexible elongate guiding instrument, while the respective other instrument may refer to an instrument to be guided along the elongate guiding instrument. Hence, in an embodiment, a) the first instrument refers to a flexible elongate guiding instrument and the second instrument refers to an instrument to be guided along the first instrument, and/or b) the second instrument refers to a flexible elongate guiding instrument and the first instrument refers to an instrument to be guided along the first instrument.

Additionally or alternatively to being flexible, the reflective guiding instrument may be articulating, i.e. comprise one or more joints with respect to which the controller may control movement of the respective instrument. The case of one of the two instruments being elongate and guiding a respective other of the two instruments by means of physical contact has been found to be of particular relevance, since in this case induced motions have been observed for an extended amount of time, i.e. as supposed to relatively short motions corresponding to collision-like incidences.

Preferably, both instruments are elongate instruments, particularly flexible and/or articulating elongate instruments. Moreover, the first instrument and the second instrument preferably form a joint, i.e. combined, instrument in which the first instrument and the second instrument are coaxially alignable, wherein the second instrument forms an outer instrument part configured to slide along the first instrument forming an inner instrument part.

The position of the first instrument, which will subsequently also be referred to as the first position, may refer to a distal tip of the first instrument, and the second position may refer to a distal tip of the second instrument. If any of the instruments is not elongate, instead of a distal tip of the respective instrument, any other distal part of the respective instrument may be considered.

Being "not elongate" shall be understood as referring to instruments having a relatively compact shape, possibly characterized by a relatively equal size in all dimensions, whereas an "elongate" instrument shall be understood as an instrument having a size in one dimension against which its size in the respective two other dimensions is relatively small or even insignificant for all practical purposes.

The term "distal" preferably refers to a part of the respective instrument that is, as measured in a longitudinal direction of the instrument away from a moving means of the instrument, relatively far or furthest away, wherein "proximal" has the opposite meaning. The moving means can correspond to a motor or a drive, for instance, or to a device mediating a manual moving action by a user. Irrespective of whether they refer to a distal tip or other distal parts of the respective instrument, the first and the second position may be determined by a detectable element of the respective instrument. The detectable element may refer to, for instance, a metal bead, ring or other shape, and/or to an electromagnetic sensor.

Both the first instrument and the second instrument may be medical instruments, wherein the controller may be configured to control a movement of the first instrument along a tubular anatomical structure. Optionally, the controller is configured to control a movement of the first instrument and the second instrument along the tubular anatomical structure in the patient's body. For instance, the first instrument may be robotically driven along the tubular anatomical structure, possibly based on a user input, while the second instrument may also be robotically driven or may be driven manually.

Movements of the first and/or the second instrument are not necessarily limited to stay within a tubular anatomical structure. Instead, for instance, the first instrument and the second instrument may be moved so as to leave the tubular anatomical structure to reach a tumor, or a body cavity where a treatment is to be applied. The position limiting indicator can be in the extra tubular location, and the exit location can be thought of as an ostium. Also such movements of the first and/or second instrument leaving the anatomical structure may be effected by the controller and/or manual manipulation. According to a particular example, the second instrument could refer to a catheter and the first instrument could refer to a guidewire of the catheter. In a typical workflow, the guidewire might first be protracted into the tubular anatomical structure. Guidewires are typically easier to navigate than catheters. Following the guidewire, the catheter, comprising a hollow body radially surrounding the guidewire about its axis, would be protracted into the tubular anatomical structure by using the guidewire as a physical guidance. For changing the catheter, i.e. for catheter exchange, which is often necessary due to limited functionalities of catheters, the guidewire should typically remain as far as possible in place, while the catheter is being retracted. Both during protraction of the guidewire and retraction of the catheter, the respective instrument can accidentally drag the respective other one with it. To suppress undesired motions in both situations, i.e. protraction of the guidewire and retraction of the catheter, both of the above indicated alternatives a) and b) can become relevant.

More generally, the controller of the control device may be configured to determine a first distance based on the first position, i.e. the position of the first instrument, and the indicator of the limiting position, wherein the first distance is indicative of a distance between the position of the first instrument and the limiting position of the first instrument, and to control the movement of the first instrument based on the first distance. Likewise, the controller may be configured to determine a second distance based on the position of the second instrument and the target indicator, wherein in the second distance is indicative of a distance between the target position and the position of the second instrument, and to control the movement of the second instrument based on the second distance. Controlling the movement of the instruments based on the first and second distance, respectively, can refer to a proportional control, for instance. That is to say, the controller may be configured to determine control signals leading to a driving force or movement speed that is proportional to the respective distance.

Both the first distance and the second distance can be determined according to a predefined distance measure, such as, for instance, a geometric, particularly a Euclidean, or a physical distance measure. These distance measures are preferably three-dimensional, i.e. measuring distances in three-dimensional space. If full three-dimensional information is not originally available, it can be recovered from two-dimensional information via calibration. For instance, if one or both of the position of the first and the second instrument is originally measurable only in two spatial dimension, which may particularly be the case when determining the respective position based on X-ray images, a respective instrument position in three-dimensional space can be determined based on the respective two-dimensional measured position and a calibration factor determined based on a calibration measurement.

An exemplary distance measure would be a measure of a length of a path or pathway, which could also referred to as an arc length. Regarding the first instrument, for instance, the controller may be configured to determine a distance between the position of this instrument and the limiting position indicated for this instrument by the corresponding indicator, and to control the movement of the instrument based on the distance, wherein the distance is optionally defined along a path or pathway. The same control can be applied to the second instrument, wherein instead of the first position and the limiting position the second position and the target position would be considered.

Hence, for instance, the first and the second distance may be determined based on a respective path determined from the respective position and the respective indicator. Concretely, a first path may be defined between the position of the first instrument and the limiting position for the first instrument, wherein the first distance may be determined along the first path. Likewise, a second path may be defined between the position of the second instrument and the target position for the second instrument, and the second distance may be measured along the second path. The first path may be a path to be taken by the first instrument, while the second path may be a path to be taken by the second instrument. In a more particular embodiment, the path may be predefined to lie along the tubular anatomical structure. In such embodiments, the controller of the control device could be configured to a) determine a first anatomical distance based on the first position, the indicator of the limiting position for the first instrument and the tubular anatomical structure, wherein the first anatomical distance is indicative of a distance between the first position and the limiting position for the first instrument along the tubular anatomical structure, and to control the movement of the first instrument based on the first anatomical distance, and/or b) determine a second anatomical distance based on the second position, the target indicator and the tubular anatomical structure, wherein the second anatomical distance is indicative of a distance between the second position and the target position for the second instrument along the tubular anatomical structure, and to control the movement of the second instrument based on the second anatomical distance.

For determining the first and/or the second distance, particularly the first and/or the second anatomical distance, the control device may comprise a structural representation providing unit configured to (or may implement corresponding instructions executed by the processor causing the control device to) provide a representation of the tubular anatomical structure and/or the first and second instrument, in which the first position, i.e. the position of the first instrument, the limiting position of the first instrument, the second position, i.e. the position of the second instrument, and the target position for the second instrument are identifiable. The structural representation is preferably determined based on the data used for instrument positioning, i.e. based on the received image including respective portions of the one or more instruments and/or the respective instrument's movement. The structural representation of the tubular anatomical structure and/or the first and second instrument may be an image, such as the image based on which it is optionally determined itself or a more schematic version of it, possibly just consisting of line segments. The structural representation can however also be a different, i.e. non-image-based representation. For instance, it can refer to numerical, parametric or any other data, which could be, but are not necessarily, used to generate an image, wherein the data may be indicative of line segments corresponding to the tubular anatomical structure and/or the first and second instrument, or of locations of pixels in an image of the tubular anatomical structure and/or the first and second instrument. The structural representation can be three-dimensional, i.e. volumetric, irrespective of a dimensionality of the image or the movement data based on which it is preferably determined.

The limiting indicator providing unit may be configured to (or corresponding instructions may cause the control device to) provide the indicator of the limiting position as a line segment, perpendicular to a part of the tubular anatomical structure in an axial cross-section thereof. Likewise, the target indicator providing unit may be configured to (or corresponding instructions optionally cause the control device to) provide the target indicator as a line segment, perpendicular to a part of the tubular anatomical structure in an axial cross-section thereof. In particular, the provided indicators can be line segments oriented perpendicular to a centerline of the tubular anatomical structure at a respective longitudinal position of the tubular anatomical structure, wherein the line segments may be provided with a length smaller or equal to a transverse extent of the tubular anatomical structure at the respective longitudinal position, i.e. so as to stay inside the tubular anatomical structure. Instead of line segments, each of the indicator of the limiting position and the target indicator could correspond, for instance, to any of a point, an arc, an area, a set of line segments, a three-dimensional volume, a circle or a rectangle.

Hence, in an embodiment, for instance, the first instrument is a medical instrument whose position is determined from a received image including a portion of the instrument, wherein the controller is configured to control a movement of the instrument along a tubular anatomical structure, wherein a portion of the tubular anatomical structure is included in the image, and wherein the representation of the indicator is provided across an imaged tubular structure. Optionally, the controller is configured such that the size of the representation of the indicator provided across an imaged tubular structure dynamically changes with the potential change of width of the imaged tubular structure.

It may be preferred that the position of the instrument to be moved is provided based on image data. For instance, the control device may further comprise an image data providing unit configured to (or corresponding instructions may cause the control device to) provide image data for an image of at least one of the first instrument and the second instrument, wherein, if the image is an image of the first instrument, the first position providing unit is configured to (or corresponding instructions cause the control device to) determine the first position based on the image, and if the image is an image of the second instrument, the second position providing unit (or corresponding instructions cause the control device to) is configured to determine the second position based on the image. The image data can particularly be fluoroscopy or other X-ray data, magnetic resonance imaging (MRI) data, ultrasound data, or other medical imaging data. Other medical image data can include, for instance, image data acquired by electrophysiological dielectric (EPD) imaging, by which the respective instrument can be traced in three-dimensional space with respect to an anatomical environment through which it moves. An imaging modality may be selected depending on the first and/or the second instrument and vice versa, such that the first and/or second instrument can be imaged, i.e. becomes visible in a respective image. This may depend, for instance, on a material of the respective instrument. Optionally, markers can be attached to an instrument to allow for visibility in images of a selected imaging modality. The position of the respective instrument may then correspond to the position of the marker. In order to increase visibility of the first and/or second instrument, also image processing measures can be taken. For instance, any of the instruments can be identified in an image and further highlighted therein for a user. The identification can be achieved by segmentation, for example, and the highlighting can correspond to overlaying visual markers on the respective instrument, particularly the position of it that is taken as a basis of movement control. In an embodiment in which the position of the first instrument is provided based on a received image of a portion of the first instrument and the movement of the first instrument is controlled based on a distance as indicated above, the limiting position indicated for the first instrument may refer to a position in the received image, and the distance may be determined based on the image.

On the other hand, at least one of the first position and the second position may be provided based on non-image-based data. For instance, when moving the respective instrument by a robot, robotic data may be used as non-image data. Based on past robotic data, such as past user inputs and/or control signals issued by the controller, information on previous movements of the respective instrument can be retrieved, and based on this information a current position of the instrument can be determined.

Moreover, also a combination of image-based data and non-image-based data may be used for determining any or both of the first and second position. In case image data are used for determining one of the first and the second position, while non-image data are used for determining the other of the first and the second position, the image data and the non-image data may be registered with each other. A registration may also be carried out in case both the first and the second position are determined based on image data, such as in case the image data used for determining one of the positions stems from a different imaging modality than the image data used for determining the other position.

If as indicated further above, a path is taken as a basis for determining a distance based on which to control a respective instrument's movement, this path may be determined based on the provided image data and/or the non-image data. Determining the path in an image may be preferred. Hence, for instance, the indicated limiting position can refer to an image corresponding to the image data, wherein the path, i.e. the path determined for controlling the first instrument, could be determined based on the image data. Similarly, for controlling the second instrument, the target position indicated by the target indicator may refer to an, or the image corresponding to the image data, wherein the path, i.e. the path determined for controlling the second instrument, could be determined based on the image data.

In a particular embodiment, the control device comprises an image data providing unit configured to (or corresponding instructions executed by the processor cause the control device to) provide image data for an image of the tubular anatomical structure, including the first instrument and the second instrument inside the tubular anatomical structure, wherein the first position, the limiting position for the first instrument, the second position and the target position for the second instrument refer to positions in the image, and wherein the controller is configured to determine the first anatomical distance and/or the second anatomical distance, respectively, as distances along the tubular anatomical structure as visible in the image.

Besides, the limiting indicator providing unit may be configured to (or corresponding instructions executed by the processor cause the control device to) provide the indicator of the limiting position based on anatomical information and/or based on a user input, such as a user input provided via a user interface.

The anatomical information may be indicative of a risk associated with the first position, i.e. the position of the first instrument, not maintaining the predetermined relation with respect to the limiting position. For instance, the indicator of the limiting position may be provided in such a way that a risk of the first instrument leaving a predefined vessel or vessel part, which can be a vessel or vessel part in which the first instrument is currently positioned, is minimized. Exemplary risk measures for this purpose may take into account a distance from the position of the first instrument to a proximal, particularly nearest proximal, ostium or bifurcation of a current vessel in which the first instrument is positioned, a diameter of the vessel, a ratio in diameter between the first instrument and the current vessel, a heuristically determined quantity, and/or a turn radius of the current vessel, including a turn radius of the current vessel with respect to a previous vessel from which the first instrument has entered the current vessel. Instead of a turn radius, also other quantities indicative of a curvature of the current vessel can be taken into account.

Providing the limiting indicator based on a user input can refer to a selection of the limiting position by a user. If the user wishes the first instrument's position to be "pinned", it may not be necessary for him/her to actually select the position anymore. Instead, he/she may just activate a dedicated mode in which the limiting position is automatically set to the current position of the first instrument. In a further control mode, which may also be activated and/or deactivated by a user, the limiting indicator providing unit may be configured to (or corresponding instructions executed by the processor causing the control device to) adapt the indicator over time. For instance, as the first instrument is being moved through a branched tubular anatomical structure, the limiting position for it may be adapted every time it has entered a new branch of the tubular anatomical structure, e.g. to a proximal position of the respective new branch or the respective preceding branching point.

Accordingly, the limiting indicator providing unit may be configured to (or corresponding instructions executed by the processor may cause the control device to) provide the indicator for the limiting position based on an imaged anatomical feature, particularly a new branch where the instrument enters into, if the instrument is moved along a tubular anatomical structure, and/or on a user input through a user interface configured to associate a user input with a location in the image and/or on stored predefined setting parameters.

Moreover, the limiting indicator providing unit may be configured to (or corresponding instructions executed by the processor may cause the control device to) provide the indicator of the limiting position based further on the position of the respective instrument for which it is provided, i.e. particularly the first position, which is the position of the first instrument. For instance, the indicator of the limiting position may indicate the limiting position for the first instrument to lie at, or just distal to, a, with respect to the first position, nearest, but preferably still proximal, bifurcation of the anatomical structure. In this way, a potential necessity to re-cannulate the first instrument into a branch of the anatomical structure after being accidentally withdrawn from it can be avoided. Navigating an instrument into a correct one of several branches branching from a bifurcation, which can be referred to as cannulation, can be the most challenging part in a navigation process carried out with the instrument.

It may be preferred that the controller is configured to control the movement of the first instrument based on a change of the first position, i.e. the position of the first instrument. In particular, the movement of the first instrument may be adapted based on the change of the first position. For example, the controller may be configured to detect when the first position does not change although the first instrument is controlled to move beyond a threshold distance, and to modify, particularly slow down, the movement of the first instrument or to trigger an alert to a user in this case. This can avoid potentially harmful jumps of the first instrument due to spring effects caused by temporary blockages. Likewise, the controller may be configured to detect when the second position does not change although the second instrument is controlled to move beyond a threshold distance, and to modify, particularly slow down, the movement of the second instrument or to trigger an alert to a user in this case. More generally, i.e. for any number of controlled instruments, the controller can be configured to detect when the position of the, i.e. the respective, instrument to be moved does not change although the instrument is controlled to move, and to slow down any movement of the instrument in this case.

Any of the indicator of the limiting position and the target indicator may be a graphical indicator, possibly displayed together with the first and/or the second instrument, or only the first and/or second position, in an image, such as an image of the tubular anatomical structure. Optionally, the respective indicator is a segment across an imaged vessel, possibly moving with a movement of the vessel. A width of the indicator may change with a change of a width of the vessel, the width of the vessel potentially changing physically due to changes in blood pressure as caused, for instance, by blood pulses or vasospasms, or virtually due to, for instance, a change in image magnification.

Moreover, the controller may be configured to increase a degree of control over the first position when a distance between the first position and the limiting position decreases. For instance, the degree of control may increase monotonically with degreasing distance between the first position and the limiting position. In particular, if the first position is determined to coincide with the limiting position, the degree of control can be maximal, such that any movement of the first instrument, particularly any motion induced upon it by a movement of the second instrument, is prevented. In a specific implementation, the controller may control the movement of the first instrument such that the first position does not cross the limiting position.

In an exemplary embodiment, the first instrument is an inner device and the second instrument is an outer device, wherein the received image includes an image of a portion of the first and second instruments and a branched intersection of a plurality of branches of the anatomical structure, including a main branch and a target branch which is branched from the main branch, and wherein the controller is further configured to maintain the inner device at a target point in a target branch of the tubular anatomical structure, when the controller causes retraction of the outer device, by further advancing the inner device by an amount compensating for the retraction of the outer device.

In a further aspect, the invention relates to an apparatus for moving a medical instrument. The apparatus comprises the control device, and additionally a drive controllable by the controller of the control device to drive the movement of the instrument to be moved, i.e. particularly the first instrument. Also the movement of the second instrument may be driven by the drive based on a control of the controller of the control device.

The apparatus may further comprise an imaging device configured to capture images of the first instrument and the second instrument. These images may be used to determine the first and the second position. Moreover, the apparatus may comprise a display device configured to display the first and the second instrument. This display device may be used by a user to determine, using his or her expertise and visual judgement, a user input to be provided via a user interface to a controller. Also the display device itself may function as the user interface. For this purpose, it may comprise a touchscreen, for instance.

In another aspect, the invention relates to a method for controlling movement of a medical instrument, wherein the method includes a) providing an indicator of a limiting position for an instrument beyond which the position of the instrument is considered as out-of-limit, b) providing a position of the instrument from a received image including a portion of the instrument and/or retrieved movement of the instrument, and c) controlling a movement of the instrument based on the indicator of the limiting position and the position of the instrument such that the position of the instrument maintains a predetermined relation with respect to the limiting position.

Furthermore, an aspect of the invention relates to a method for moving a medical instrument, the method including controlling the instrument in accordance with the previously indicated method for controlling movement of a medical instrument, and driving the movement of the first instrument accordingly.

Further aspects of the invention relate to a computer program for controlling movement of a medical instrument, wherein the program comprises instructions causing the control device to execute the method for controlling movement of a medical instrument, and to a computer program for moving a medical instrument, wherein the program comprises instructions causing the apparatus from above to move the instrument in accordance with the above method for moving a medical instrument, if the program is executed on a computer controlling the apparatus.

It shall be understood that the control device of claim 1, and the apparatus of claim 17 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
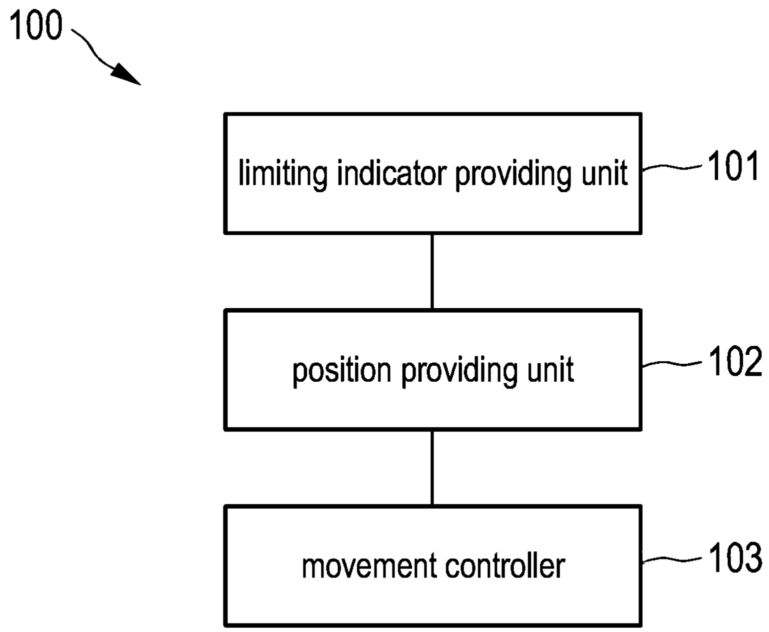
FIG. 1 shows schematically and exemplarily a control device for controlling movement of a medical instrument.

FIG. 1 shows schematically and exemplarily a control device 100 for controlling movement of a medical instrument. The control device 100 comprises a limiting indicator providing unit 101 configured to provide an indicator 12 of a limiting position for an instrument 10. The indicator 12 can also be referred to as a limiting indicator. Beyond the limiting position, the position of the instrument 10 is considered out-of-limit. Moreover, the control device 100 comprises a position providing unit 102 configured to provide a position 11 of the instrument 10 from a received image including a portion of the instrument and/or retrieved movement of the instrument, and a controller 103 configured to control a movement of the instrument 10 based on the indicator 12 of the limiting position and the position of the instrument such that the position of the instrument maintains a predetermined relation with respect to the limiting position.

Figure 2A:
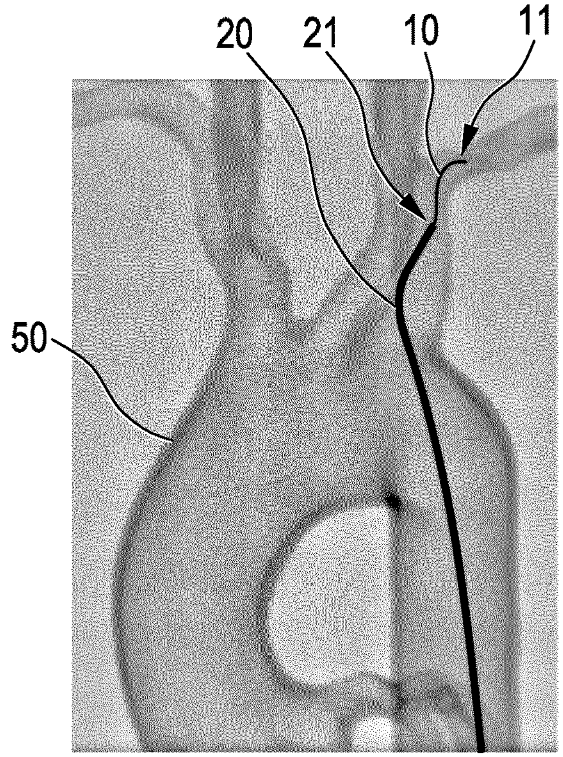
FIG. 2 shows, in its four parts given by FIG. 2A to FIG. 2D, schematically and exemplarily different stages during a catheter exchange.

FIG. 2A to FIG. 2D illustrate a control mechanism implemented by the control device according to a particular embodiment in its application to the situation of catheter exchange. In this embodiment, the instrument 10 is a guidewire for a medical catheter. The guidewire is considered a first medical instrument, while the catheter is considered a second medical instrument 20. FIG. 2A shows a state in an endovascular procedure in which a target position inside a vasculature of a patient has been reached by the guidewire and the catheter. In order to reach the target position, the guidewire has first been inserted into the patient and through the vasculature, whereafter the catheter has been inserted by help of the guidewire, namely by sliding along it. As is often the case in endovascular procedures, once the target position has been reached, an exchange of devices is required. In the illustrated case, the catheter needs to be exchanged for a new one, meaning that the present catheter needs to be removed from the body and a new one needs to be inserted over the guidewire. Since the catheter is in physical contact with the guidewire, its retraction, or pullback, along the guidewire can lead to an accidental withdrawal or other induced motions of the guidewire. If the induced motion becomes too large, i.e. if the guidewire is accidentally repositioned too far from its initial position prior to commencement of the exchange process, it may no longer be possible to reach the target position with the new catheter to be installed. It may then be necessary that the guidewire is corrected in position again, which can increase the procedure time beyond an expectable degree and/or lead to other medical complications. Particularly in emergency situation such as strokes, any delay or other procedural complication can have serious health consequences for the patient. In fact, the induced motion can also in itself become dangerous for the patient. For instance, snapping motions of elastic guidewires may be triggered when a distal part thereof is accidentally pulled out of a vessel branch.

In the illustrated embodiment, the control device 100 further comprises a target indicator providing unit configured to provide a target indicator 22, the target indicator 22 being indicative of a target position for the second instrument 20, which is in this case the catheter, and a second position providing unit configured to provide a second position 21, the second position being a position of the second instrument 20, i.e. the catheter. Moreover, the controller 103 is in this case configured to not only control the movement of the first instrument 10, i.e. in this case the guidewire, but also a movement of the second instrument 20 being the catheter, wherein the movement of the second instrument 20, i.e. the catheter, is controlled based on the target indicator 22 and the second position 21 such that the second position 21 approaches the target position.

From FIG. 2A to FIG. 2D, the catheter is retracted from an initial position towards a target position, the latter being indicated by an intersection of the target indicator 22 with the line as which the catheter appears in the image. As the relevant position of the catheter based on which the movement is controlled, its tip 21 is assumed. While the tip 21 of the catheter 20 moves from its initial position towards the target position along the guidewire 10, the tip 11 of the guidewire 10 is accidentally withdrawn, which can be considered an induced motion. This is noticed by the controller 103 by virtue of being provided with the guidewire's tip position 11 by the position providing unit 102, which may use artificial neural network-aided image segmentation for this purpose. Moreover, the limiting indicator 12 provided by the limiting indicator providing unit 101 is, in the illustrated embodiment, a line segment 12 similar to the line segment 22 corresponding to the target indicator 22 for the catheter, wherein, however, the line segment corresponding to the limiting indicator 12 is located distal relative to the target indicator 22. The predetermined relation which the position of the guidewire 10 being the first instrument is to maintain with respect to the limiting position indicated by the indicator 12 could in this case be formulated as the condition that a distance between the guidewire's tip position 11 and any position on the line segment 12 should stay larger than zero, preferably larger than zero by a predetermined margin. In this way, as will be appreciated from FIG. 2C and FIG. 2D, the controller 103 can counterbalance or inhibit a withdrawal of the guidewire by the retracted movement of the catheter if it notices that the predetermined relation is at risk of not being maintained, namely if it is determined that the tip of the guidewire is about to cross the line segment corresponding to the indicator 12.

A guidewire like the one shown in FIG. 2A to FIG. 2D can be understood as an example of a flexible elongate guiding instrument by which a second instrument like the catheter also illustrated by FIG. 2A to FIG. 2D can be guided. The guidance is in this case facilitated by means of physical contact between the guidewire and the catheter, meaning that the catheter slides along the guidewire. Typically, the catheter, which can itself also be understood as a flexible elongate instrument, would be designed in a tube or sleeve shape having a diameter sufficient to allow the catheter to slide over the guidewire in an axial direction while radially surrounding the guidewire. The guidewire may be specifically designed so as to be easily navigable. This allows the catheter, which may by itself be less easily navigable than the guidewire, to be navigated to a treatment site in a patient's body by pushing it along the guidewire. A guidewire could also be regarded as an inner instrument with respect to the catheter, wherein the catheter could be regarded as an outer instrument with respect to the guidewire being the inner instrument.

It will be understood that, while movements of the catheter can induce motions of the guidewire, also the reverse situation may happen, i.e. that movements of the guidewire induce motions of the catheter. While the former situation may happen, for instance, during retraction of the catheter for catheter exchange, the latter situation may arise, for instance, if the guidewire is further protracted or if it is retracted while the catheter has already been partially or completely slid over the guidewire. Moreover, both of the two instruments may be moved simultaneously, in which case their respective movements induce motions upon each other. Particularly in such a case, indicators for limiting positions and target indicators may be defined for each of the two instruments.

While a guidewire and a catheter are examples of medical instruments, it will be understood that the control mechanisms described with respect to the illustrated embodiment are equally applicable to other instruments. In particular, the instruments controllable by the controller 103 are not necessarily moved along a tubular anatomical structure in a patient's body, such as along vessels as illustrated by FIG. 2A to FIG. 2D. Instead, the controller 103 may be configured to control a movement of the instruments in other environments as well.

Movements of the one or more instruments may be controlled by the controller 103 based on their respective position and the respective limiting position indicator and/or target indicator. In the illustrated embodiment, which exemplifies the case that the catheter 20 is being retracted while the guidewire should remain in place, the controller 103 is configured to determine a first distance based on the guidewire's tip position 11 in the image, as provided by the position providing unit 102, and the indicator 12 corresponding to the distal line segment visible in the image and being provided by the limiting indicator providing unit 101, wherein the determined distance is indicative of a distance between the position 11 of the tip of the guidewire and the limiting position for the guidewire 10. The latter is given in this case by the axial position along the vessel branch on which the line segment 12 appears in the image.

In principle, many distance measures could be chosen for the distance determination. For instance, the shortest two-dimensional Euclidean distance between the tip of the guidewire as it appears in the image and points on the line segment 12, or an intersection thereof with the vessel structure, could be considered. It may however be preferred that an anatomical distance measure is applied, such that the controller 103 determines an anatomical distance between the position 11 of the tip of the guidewire and the position of the indicator 12. An anatomical distance may be understood as a distance along an anatomical structure in which the one or more instruments are being moved, such as a vessel structure in the illustrated embodiment. Hence, an anatomical distance determination may need to be further based on the respective anatomical structure. Anatomical distances may more accurately reflect the physically possible pathways for the instruments in the anatomical structure. For instance, in the case of very curved vessels, the tip of a guidewire may be located "around the corner" as seen from a limiting indicator like the line segment 12, such that a Euclidean distance would correspond to a pathway of the catheter tip "cutting the corner", i.e. leaving the vessel.

According to one particular anatomical distance measure applicable in the illustrated embodiment, an arc length of the curve as which the guidewire 10 appears in the image would be taken as a basis for controlling the movement of the guidewire 10, wherein the arc length would be measured between the guidewire's tip position 11 and the point of intersection between the curve as which the guidewire 10 appears in the image and the line segment 12 corresponding to the indicator of the limiting position for the guidewire 10. Hence, in this particular case, the only position indicated by the indicator of the limiting position and entering the movement control would be the position, i.e. the location, of the point of intersection. It should be realized that this particular distance measure would yield results that can come the closer to a Euclidean distance measure the straighter and/or shorter the part of the guidewire extending beyond the line segment 12 is or becomes. Whether anatomical or not, applicable distance measures include three-dimensional distance measures. Three-dimensional distances can be determined, for instance, based on three-dimensional image data.

Figure 2B:
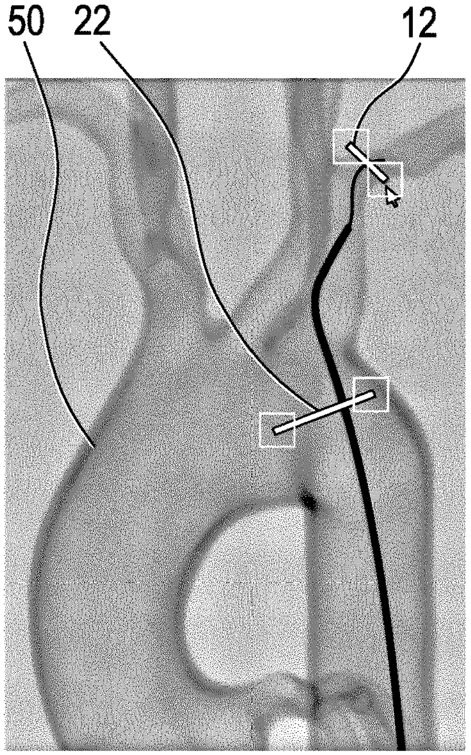
Figure 2C:
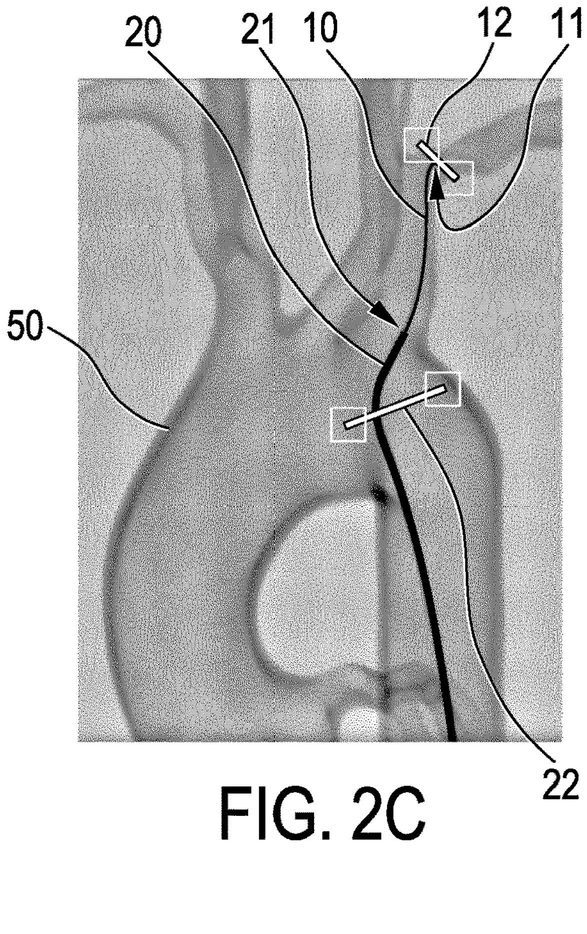
Figure 2D:
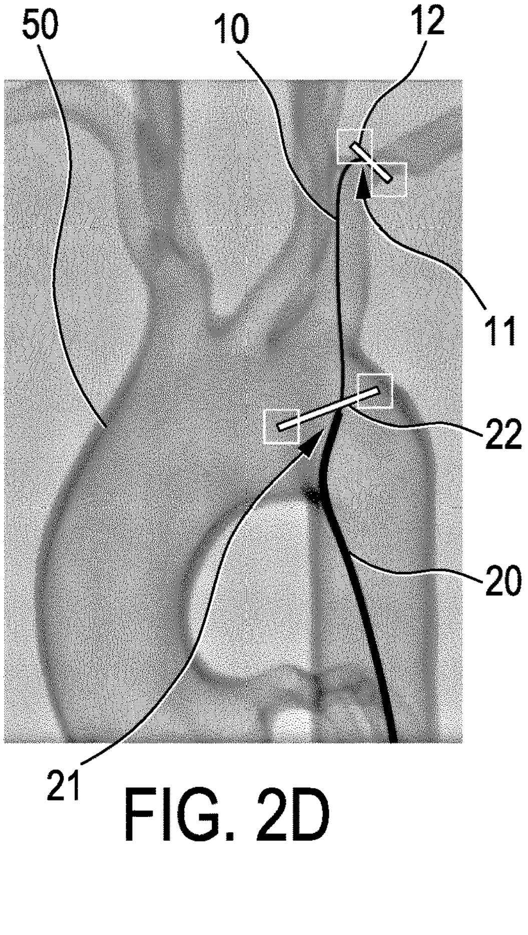

In the illustrated embodiment, in order to retract the catheter 20, the controller 103 is configured to determine a second distance based on the position of the catheter's tip 21 as provided by the second position providing unit based on the image, and the target indicator 22 corresponding to the larger, proximal line segment seen in FIG. 2B to FIG. 2D. The second distance can be determined based on the same or a different distance measure as compared to the first distance, i.e. when compared to the catheter and the line segment 22. The second distance is used as a basis for controlling the movement of the catheter 20.

Images like those shown in FIG. 2A to FIG. 2D can be acquired by an imaging modality and thereafter provided in terms of image data to the control device 100, particularly the controller 103. For this purpose, the control device 100 may comprise an image data providing unit configured to provide the image data. One or more images may be acquired, and thereafter provided in terms of image data by the image data providing unit, of only the instrument to be moved by the controller 103, or also of one or more further instruments whose movements may induce motion upon the instrument to be moved. In the illustrated embodiment, both instruments, i.e. the guidewire 10 and the catheter 20, are imaged in a single, common image. In this case, spatially two-dimensional X-ray images are collected over time, wherein FIG. 2A to FIG. 2D each show one instant in time. Apart from X-ray, different imaging modalities may be used, such as MRI or ultrasound, for instance.

For any instrument being imaged, the instrument's position may be determined at least in part based on the image, i.e. the image data corresponding to the image. Concretely, for instance, the position of the tips of the guidewire and the catheter in the images shown in FIG. 2A to FIG. 2D may be determined to just correspond to the tips' pixel positions in the images. The positioning of the instruments may be carried out by the controller 103 also based on non-image data, such as past control data from which past movements can be retrieved. However, an exclusively image-based positioning of the instruments may, as in the illustrated embodiment, often be already accurate enough for a reliable movement control.

As explained above, in FIG. 2A to FIG. 2D, the first and the second distance, i.e. the distances based on which the movement of the guidewire 10 and the catheter 20 are controlled, respectively, could be approximately equal to the length of the portion of the respective instrument that extends, as viewed from a proximal to a distal side, beyond the respective line segment 12, 22. These lengths, which could be understood as anatomical distances since they naturally lead along the vessel structure, can be measured based on the image data by, for instance, integration along the respective instrument as visible in the image. Such an integration is hence naturally also carried out along the vessel structure, whereas in a formula for these lengths no explicit reference any anatomical structure would be needed. If, for instance, the guidewire 10 is represented internally as a set of consecutive segments, the arc length based on which the distance used for controlling its movement can be measured in terms of the sum of the lengths of the segments extending distally beyond the limiting indicator 12. Should the guidewire 10 have been withdrawn so far that it no longer intersects the indicator 12, then the closest distance between its tip position and any point on the indicator 12 could be used for controlling the guidewire such that its tip moves back past the indicator 12 again. Hence, the distance measure used to determine the distance based on which the respective instrument is controlled may depend on the instrument's position relative to its respective limiting positing and/or target position.

The indicator 12 is provided by the limiting indicator providing unit 101 based on anatomical information. The anatomical information may again be derived from image data, particularly the image data based on which also the position of one or more of the instruments has been determined. As illustrated by FIG. 2A to FIG. 2D, for instance, the indicator 12 may indicate the limiting position with respect to a part of the anatomical structure in which the first instrument is moved. Moreover, the indicator 12 may be adapted to a geometry of the anatomical structure. For instance, given a preliminary limiting position for a first instrument like the guidewire 10, which may be indicated by a user or correspond to a fixed, predefined position, the indicator 12 may be determined by the limiting indicator providing unit 101 to lie at roughly this preliminary position, but such that it indicates a limiting position for all physically possible pathways of the first instrument passing the rough preliminary position. In the illustrated case of the indicator 12 corresponding to a line segment in an image, for instance, a user may choose a rough position in the image where he/she intends the indicator 12 to be placed, wherein then the limiting indicator providing unit 101 could fix the corresponding line segment to have a location at an extent so as to fully close off the vessel in a region closest to where the user has preliminarily intended the indicator 12 to be.

Moreover, the limiting indicator providing unit 101 may be configured to provide the indicator 12 based further on the position of the first instrument 10. In this case, a user input may no longer be needed, since the anatomical information and the position of the first instrument 10 may, according to a possibly predefined criterion, uniquely determine where the indicator 12 is to be placed. For instance, as will be appreciated from FIG. 2A and FIG. 2B, by requiring the indicator 12 to correspond to a line segment positioned between a current tip position 11 of the guidewire and the closest branch of the vessel structure proximal to the current tip position 11, and moreover to lie transverse to a longitudinal axis of the vessel segment in which the guidewire tip 11 is positioned, the line segment 12 is substantially fixed.

Optionally, a length of any line segments corresponding to the indicator 12 and the target indicator 22 can be chosen to comply with a dimension of the anatomical structure at a position of the respective indicator, wherein the dimension is preferably chosen to be measured in a direction transverse to a movement direction of the respective instrument. The line segments may then be displayed as an overlay over the image in which also the one or more instruments are displayed in the anatomical structure. In FIG. 2A to FIG. 2D, for instance, the indicating line segments 12, 22 extend across the respective vessel sections, such that any movement of the respective instrument 10, 20 is likely or almost certain to cross the respective line segment 12, 22 some time. In the case of the line segment 22 corresponding to the target indicator for the catheter 20 during retraction, the diameter of the vessel section proximal to the target indicator's position has been extrapolated to some extent, such that the line segment 22 closes off the imaginary extension of the proximal vessel section in a distal direction. The line segments 12, 22 may also be moved, and/or changed in size, according to temporal changes in the anatomical structure. For instance, the line segments 12, 22 may be moved with the vasculature motion and/or modified to comply in length with a temporally changing width of the vasculature, as causable by blood pulses, for instance.

The limiting position indicated by the indicator 12 could be regarded as a "pinning" position, and the indicator 12 itself could be regarded as a "virtual anchor" that "anchors" or "pins" the first instrument, i.e. the guidewire 10 in the illustrated embodiment, to a predefined position, at least if it approaches this position from, for instance, its distal side. As indicated above, the indicator 12 can be determined automatically or semi-automatically, i.e. automatically up to being based on a user input, for instance. While it may be defined relative to anatomical information derived from an image, preferably an image acquired while the instrument is being moved, such as during a medical procedure, the indicator 12 may also be generated from a preoperative model of the anatomical structure in which it is to be moved.

In some other embodiments, a guidewire may be actively anchored to a location. For example, when the guidewire is in a side branch while the catheter is in the proximal larger branch, the motion of the catheter may begin to retract the guidewire. This presents a challenge in manual manipulation because even a skilled professional needs to manipulate both of the interventional devices in four degrees of freedom simultaneously with only two hands. Using locations of the interventional devices in images, the robotic device may counteract this by advancing the guidewire relative to the catheter such that the guidewire maintains its depth in the side branch. This is accomplished by active guidewire servoing, with the feedback metric being the location of the tip of the guidewire inside the side vessel. When the tip of the guidewire is retracting due to external forces such as catheter motion, the guidewire may be automatically advanced in proportional to the retraction amount from the initial position. This minimizes the movement of guidewire escaping the cannulated side branch. In other embodiments, the guidewire may be further extended into the side branch to provide additional stabilization.

The controller 103 may also advance the inner device by a distance past the outer device, while keeping the outer device static. The controller 103 may servo-control the robotic device to retract the outer device by a distance relative to the inner device, keeping the inner device static. The controller can also retract the inner device relative to the outer device. The controller 103 may actively advance and retract the inner device relative to the initial position of the tip of the inner device relative to the image. In this way, the controller 103 may anchor the inner device to the vessel/branch. Advancing the inner device past the outer device may be performed when the controller 103 is retracting or rotating the outer device.

In some other embodiments, a guidewire position in a cannulated vessel may be slipping, and when this is recognized, the movement of the catheter may be stopped automatically and a new maneuver suggested. Additionally, when the catheter is not rotated in the correct orientation to be facing the opposite direction of the cannulated vessel, the incorrect orientation may be detected and communicated to the user along with a suggested correction. Alternatively, the correction may be automatically implemented once the incorrect orientation is detected. As a result, the guidewire may be actively anchored to the vessel by automatically correcting the catheter orientation.

Furthermore, while the indicator 12 and the target indicator 22 may be graphically represented for display to a user in terms of line segments, they could also be graphically represented differently, such as by circles, broken line segments, rectangles, areas, or volumes, for instance. More complex forms like circles, areas or volumes can be constructed from line segments. The graphical representation of the indicators 12, 22 can correspond to their internal representation in which they are provided as input to the controller 103. The indicators 12, 22 can also comprise textual labels, glyphs and/or animations, some of which may dynamically represent the distance measure, or generally a respective metric, based on which the movement of the first and the second instrument is controlled, i.e. which may be actively considered for robot motion.

However, the graphical representations chosen for the indicators 12, 22 could also be simplified versions of more complex representations defined only internally by the control device 100. For example, a rectangular area can be used to define a desired region to keep an instrument like the guidewire pinned in, wherein the region be would more accurately defined as being bounded by vessel walls and additionally two lines across the vessel at an axial, i.e. vessel-axial, distance to each other. It is understood that examples like the latter generalize to three-dimensional graphical representations by, for instance, generalizing a rectangle to a cube or a cylinder or a line segment to a square or a disc.

The controller 103 may be configured to control the movement of the one or more instruments by providing control signals as output, wherein the control signals are interpreted by a drive, which could also be regarded as a motor and could comprise, for instance, a servo system, so as to effect the respective movements. In such a configuration, particularly due to the respective environment in which the one or more instruments are moved, the actual movements effected may not correspond to the intended movements corresponding to the control signals provided as output by the controller 103. Such a mismatch between intended and actually effected movements may be identified in images acquired of the instruments while being moved, and precautionary measures can be taken in order to decrease risks associated with such a mismatch. For instance, if the controller 103 controls an instrument so as to move, but no movement of the instrument is observed in the acquired image, the controller 103 could decrease the speed at which movement of the instrument is to be effected, such as by the drive. This can decrease the risk of spring effects potentially generating unwanted large displacements of the instrument. More generally, a control algorithm carried out by the controller 103 may take into account slacks observed in an instrument to be moved. In other words, the controller 103 may be configured to detect when the position 11 of the guidewire tip does not change even though the guidewire 10 is controlled to move, and slow down any movement of the guidewire 10 in this case. Moreover, the controller 103 may be configured to detect when the position 21 of the catheter tip does not change even though the catheter 20 is controlled to move, and to slow down any movement of the catheter 20 in this case.

Figure 3:
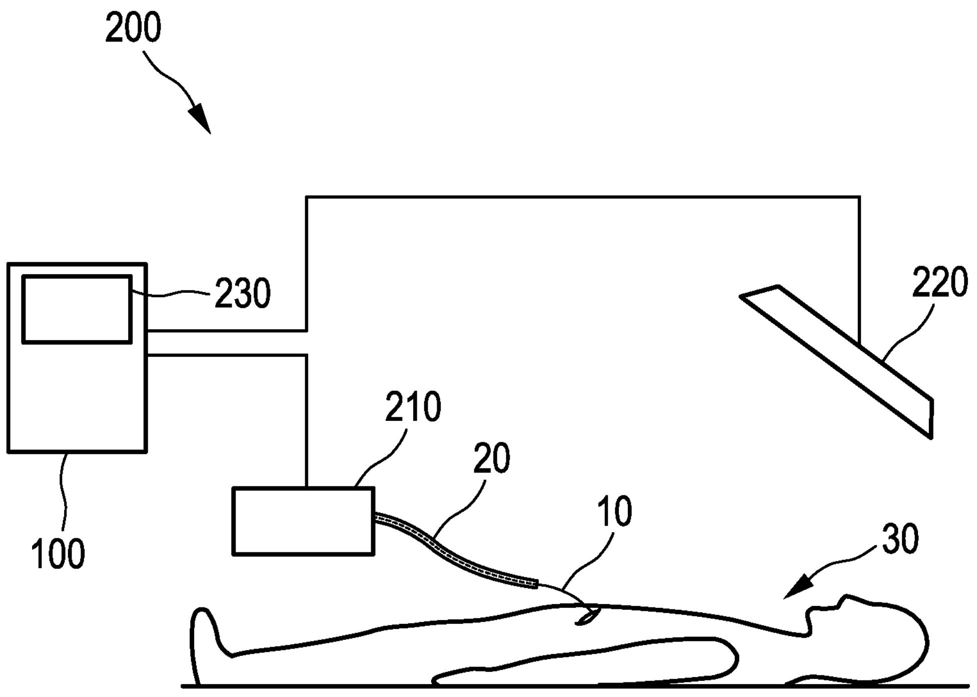
FIG. 3 shows schematically and exemplarily an apparatus for moving a medical instrument.

FIG. 3 shows schematically and exemplarily an apparatus 200 for moving one or more medical instruments like the guidewire 10 and the catheter 20 from above. The apparatus 200 comprises the control device 100 and a drive 210 controllable by the controller 103 of the control device 100 to drive the movement of the one or more medical instruments. As illustrated, the apparatus 200 further comprises an imaging device 220 that is configured to capture images of the one or more instruments. The apparatus 200 also comprises a display device 230 configured to display the one or more instruments. In particular, the images may be acquired by the imaging device 220 during an ongoing medical procedure carried out using the one or more instruments 10, 20, wherein the images may be displayed on the display 230 to a user of the one or more instruments. Based on the displayed images and possibly further graphical elements on the display 230 as determined by the control device 100, the user may provide a user input, such as via a user interface of the control device, which may correspond to the display 230 itself, wherein a control of the instruments, mediated by the drive 210, may be carried out based on the user input. In the example of FIG. 3, the medical procedure could be, for instance, an endovascular procedure on a patient 30.

Figure 4:
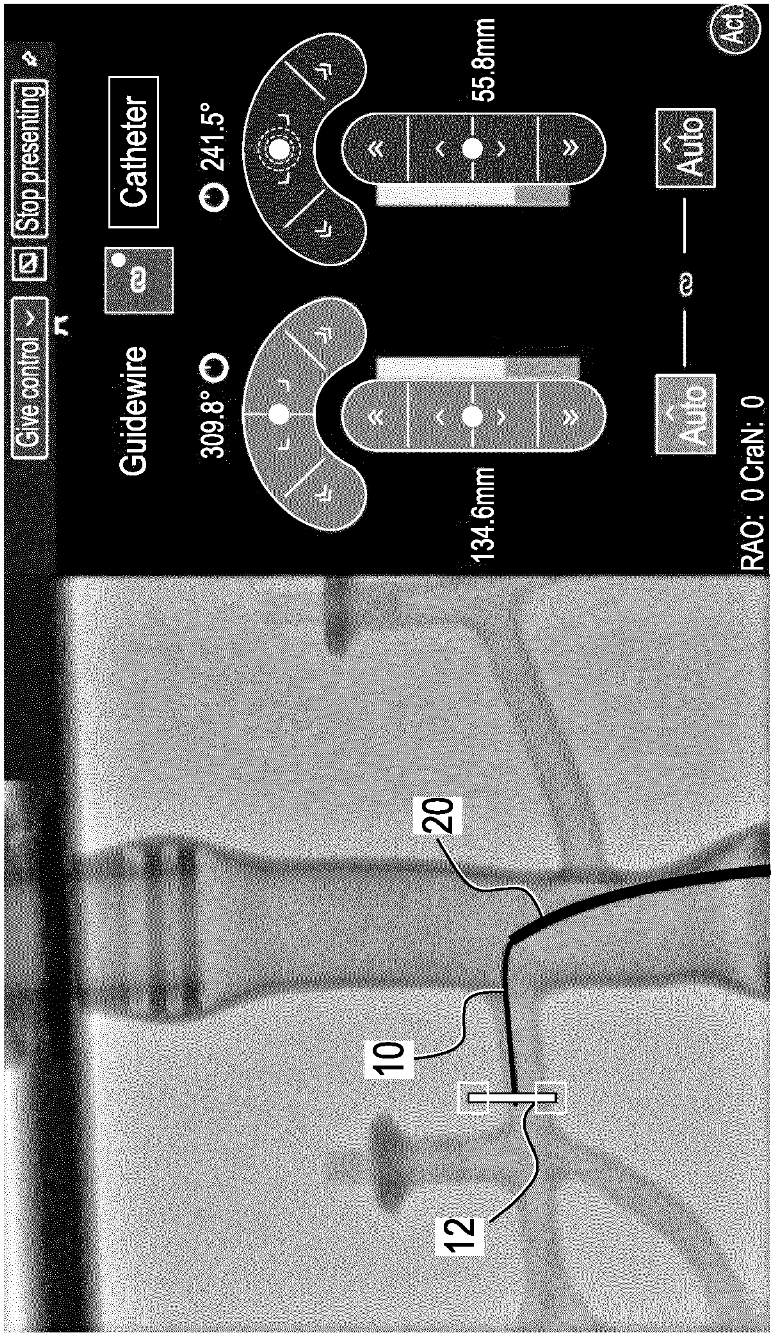
FIG. 4 shows schematically and exemplarily a display including a user interface for controlling movement of a medical instrument.

FIG. 4 shows schematically and exemplarily a display screen displayable on the display device 230 of the apparatus 200 illustrated by FIG. 3. In the left part of the display screen, an image of a guidewire 10 and a catheter 20 representing two medical instruments inside, i.e. inserted in, a tubular test structure can be seen, wherein a line segment corresponding to an indicator 12 of a limiting position has been placed in a left arm of the test structure for the guidewire 10. The image shows a state in which, for test purposes, the catheter 20 has been rotated while being retracted in order to perturb the guidewire 10. Due to the controller 103 controlling the movement of the guidewire such that the guidewire maintains a predetermined relation with respect to the limiting position indicated by the line segment 12, thereby virtually "anchoring" the guidewire tip, the attempt of perturbing the guidewire is not successful.

In the right part of the display screen shown in FIG. 4, a user interface is presented via which a user may provide control inputs for the guidewire 10 and the catheter. For each of the two instruments, the user may demand the respective instrument to be moved forward or backward, i.e. to be protracted or retracted with one of two predefined speeds (single arrow or double arrow), and to rotate around its longitudinal axis either clockwise or anticlockwise, again with one of two predetermined speeds (single arrow or double arrow). For each of the instruments, a distance indicative of how far they are inserted into the tubular structure and an angle indicative of their rotation state is displayed. Moving the instruments by use of the arrow buttons so as to explicitly effect particular translational and/or rotational movements could be regarded as a semi-automatic control. In contrast, by pressing the "Auto" buttons shown in FIG. 4, a user can initiate an otherwise fully automatic movement of the respective instrument, wherein the initiated movement can correspond to a movement of the respective instrument to a previously indicated target position, particularly while limiting a movement of the respective other instrument to an indicated limiting position. For safety purposes, the user has to press the respective "Auto" button continuously to keep the movement going. In its upper part, the user interface shown in FIG. 4 comprises a button for linking a movement of the two instruments to be controlled (indicated by two interlocked chain elements). If this button is clicked, clicking either of the "Auto" buttons triggers an automatic movement of both instruments.

Figure 5:
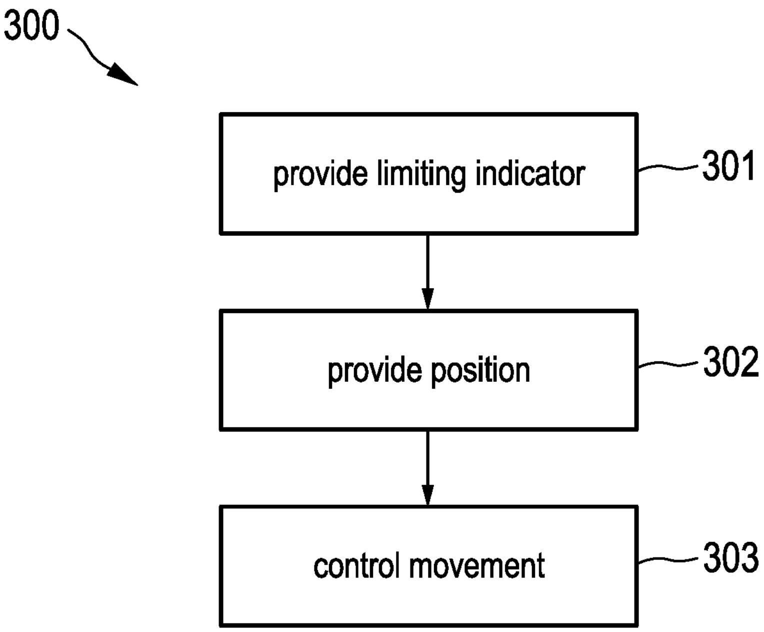
FIG. 5 shows schematically and exemplarily a method for controlling movement of a medical instrument.

FIG. 5 shows schematically and exemplarily a method 300 for controlling movement of a medical instrument, wherein the method includes, in a step 301, providing an indicator 12 of a limiting position for an instrument 10 beyond which the position of the instrument 10 is preferably considered as out-of-limit. In a step 302 of the method 300, a position 11 of the instrument 10 is provided from a received image including a portion of the instrument and/or retrieved movement of the instrument. Furthermore, the method 303 includes a step 303 of controlling a movement of the instrument 10 based on the indicator 12 of the limiting position and the position 11 of the instrument 10 such that the position 11 of the instrument 10 maintains a predetermined relation with respect to the limiting position.

Navigating endovascular instruments under fluoroscopic guidance is inherently challenging and any delays and complication can have serious health consequences for the patients in emergency situations such as stroke. Once a target location inside the vasculature is reached, an exchange of instruments is often required. During the exchange process (e.g., removing a current catheter and installing a new one over a guidewire), one or mode instruments can be accidentally dislodged (guidewire is retracted accidentally, for instance) from the target position, requiring a repeat of the navigation process and thus leading to increase in procedure time and/or complications. It has been found, inter alia, that robotically controlled instruments and image interpretation can be leveraged in a closed-loop controller to provide a reliable and automatic means to move or exchange instruments while keeping one or more of them in a desired target position inside vessels, effectively pinning the instruments to the vessel location.

In a preferred embodiment, active stabilization of the tip of a instrument in a desired target position inside a vessel can be achieved, even if another instrument is retracted, thanks to the following system (device or apparatus) for controlling coaxial elongated instruments, the system comprising a) an imaging unit arranged to provide a 2D X-ray image including imaged coaxial elongated instruments, wherein the coaxial movable elongated instruments include an inner instruments (guidewire) and an outer instruments (catheter), b) a unit for providing a limitation, configured to provide a line ("limitation line") overlaid on and crossing the imaged inner instrument (or the imaged outer instrument) such that the tip of the inner instrument (or of the outer instrument) is beyond the limitation line—this may also be referred to as a "virtual anchoring", c) a unit for image analysis, configured to identify, in the image, and during the motion of the inner and/or the outer instrument, whether the tip of the inner instrument (or of the outer instrument) is crossing or is approaching the limitation line, and to provide a corresponding output information, and d) a (robotic) controller arranged to drive the inner instrument (or of the outer instrument) and configured to adapt the motion of the inner instrument (or of the outer instrument) based on the output information, such that the tip of the inner instrument (or of the outer instrument) stays as much as possible beyond the limitation line. As described above in more detail, the limitation line can be adapted in length to and overlaid across a width of an imaged vasculature, and be moved with a vasculature motion detected in the image. Moreover, the limitation line can be provided through a user interface, or automatically by the system based on anatomical features (e.g. aperture of a vessel).

Optionally, the limitation providing unit is configured to provide a second limitation line (overlaid on and crossing the imaged outer instrument (or the imaged inner instrument) such that the tip of the outer instrument (or of the inner instrument) is beyond the limitation line, and the image analyzing unit is configured to identify, in the image, and during the motion of the inner and/or the outer instrument, whether the tip of the outer instrument (or of the inner instrument) is crossing or is approaching the second limitation line, and to provide a corresponding second output information. The controller may then be arranged to drive the outer instrument (or of the inner instrument) and to adapt the motion of the outer instrument (or of the inner instrument) based on the second output information, such that the tip of the outer instrument (or of the inner instrument) stays as much as possible beyond the limitation line. This might be particularly useful to require retracting movement of the catheter to the second limitation line (robotically controlled) while keeping the guidewire at the first limitation line. Particularly the limitation line for the instrument being retracted can also be regarded as a target line, since a retraction up to this line may be desired.

In a particular example, the system could be a robotic system for instrument navigation in neurovascular procedures. A particular target location could in that case be, for instance, the left vertebral artery of a patient. A controller of the system, which could also be regarded as a control device, might, in an embodiment, follow a control flow as follows: A.) The user selects "catheter exchange" on the user interface and an X-ray image is taken, B.) the system automatically creates target locations in the X-ray image from the device tracking information—one for catheter (distal to location where catheter exits image) and one for guidewire (at the current guidewire tip location, perpendicular to distal section), represented by line segments. The user can adjust these through a GUI. The user presses a button or display region representable by "X-ray/robot enable" and the robot automatically servoes the two devices independently to their respective target with live fluoroscopy for feedback control, C.) the robot continues to servo the catheter by retracting the catheter to the catheter's target, and D.) the catheter retraction completes. During the retraction of the catheter, the guidewire tip may be retracted to its own target. Over the whole or parts of the workflow, an incorporation of respective visual cues on a corresponding fluoroscopy image allows a physician to clearly monitor the location of the guidewire tip inside the catheter.

If image-based, the feedback control method to move the instruments can use Euclidean geometry in the image space. The instruments in the images can, for instance, be segmented and represented as ordered line segments, just like the respective limitation or target lines. The control objective can then be to move one of the instruments as close as possible to a target line. The target line could correspond to the distal end of the other instrument (tip). However, any portion of the instrument can be used to calculate, for instance, the 2D Euclidean distance between the closest point on the target line to the closest point on the instrument to be moved. This distance can then be used to protract the instrument to reach the line. In the case when the instrument crosses the target line segment, the length of the instrument past the intersection is preferably used as the metric to retract the instrument. A dead-zone tolerance can be used to minimize dithering about the target line.

For the case of guidewire stabilization, the distances to the target can be relatively small, thus servo motions will be relatively small, such that the instrument appears static or "pinned". But for the use case of catheter retraction, the motions will likely be fast to reach the target, since the target line is relatively far from the tip of the catheter.

In a preferred embodiment, the controller, or a controlled robot, "pins" the guidewire while it also retracts the catheter to be exchanged. However, alternative combinations are also possible: e.g., catheter pinned, guidewire retracted, or other combination when three or more instruments are involved. While a fully automatic control over all instruments is possible, also a user can be included in the control loop. For instance, a user may manually control one or more instruments while the robot is controlling the other. In an example, once the guidewire target(s) are defined, the user is able retract the catheter (manually or robotically) while the robot is actively "pinning" the guidewire to the target location in the image. In case of a robotically controlled catheter, the degrees of freedom of the catheter can be limited to retraction or rotation only, or both could be allowed. In the case where the guidewire is rapidly moving away from the target location, the velocities of the catheter controller could be lowered to improve target stabilization, of the guidewire. An extension of this considers the type of motion that is applied by the user and compensates for potential big changes in the length/position of the guidewire, for example fast rotations of a curved catheter.

Although the above embodiments mainly related to medical applications, it will be understood that they generalize to the control of non-medical instruments, particularly in environments different from tubular structures like vasculature in a patient.

Moreover, while the above embodiments mainly referred to cases of one or two instruments being controlled, any other number of instruments could be controlled. That is to say, indicators of a limiting positions and/or a target position could be provided for a plurality of instruments, wherein the controller of the instruments may be configured to control the plurality of instruments based on the indicators. In particular, motions induced upon more than one instrument by an environment and/or more than one other instrument could be balanced or inhibited by providing corresponding indicators, which could be referred to as induced motion limiting indicators, for more than one or two instrument. Along with the induced motion limiting indicators, target indicators could be provided for the plurality of instruments, such that the plurality of instruments could also be controlled to move towards respective target positions.

In fact, the control of the one or more instruments is also not limited to being position-based, particularly not to being only position-based. Additionally or alternatively, for instance, velocities of the instruments and/or forces on the instruments may be taken into account. Therefore, in particular, an indicator of a limiting position provided for a respective instrument could indicate the limiting position for this instrument also indirectly via other quantities. For instance, the limiting position may be indirectly defined as the position in which the instrument has a predefined limiting velocity or in which a predefined limiting force acts upon it. Likewise, the target indicator for a respective instrument may indicate the target position for this instrument only indirectly via other quantities like the instrument's velocity or a force on the instrument, such that the target position could be indirectly defined as the position in which the instrument has a predefined target velocity or in which a predefined target force acts upon it. Correspondingly, additionally or alternatively to a position providing unit for providing the position of the respective instrument, a respective velocity and/or force providing unit may be included in the control device. The predetermined relation to be maintained by the respective instrument being controlled could then also be indirectly defined, namely via the other quantities, such as in terms of a limiting force or velocity, or a target force or velocity, et cetera.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

As used herein, a providing unit can be a receiving unit configured to receive a respective quantity from another unit or device, and to provide the received quantity. However, a providing unit can also be a storage in which a previously measured or otherwise acquired quantity has been stored and from which this quantity can be retrieved for providing the same. A providing unit also can be or comprise the unit or device which has previously measured or otherwise received the quantity. Before providing a previously received or stored quantity, the quantity may be processed by the respective providing unit.

Procedures like the providing of indicators and positions, the control of movements, et cetera, performed by one or several units or devices, can be performed by any other number of units or devices. These procedures can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

A control device for controlling movement of a medical instrument is presented. The control device comprises a limiting indicator providing unit configured to provide an indicator of a limiting position for an instrument beyond which the position of the instrument is considered as out-of-limit, and a position providing unit configured to provide a position of the instrument from a received image including a portion of the instrument and/or retrieved movement of the instrument. The control device further comprises a controller configured to control a movement of the instrument based on the indicator of the limiting position and the position of the instrument such that the position of the instrument maintains a predetermined relation with respect to the limiting position. This allows for an improved movement control for medical and other instruments.

One and/or other of the "units" as herein used (e.g. "limiting indicator providing unit", "position providing unit", "target indicator providing unit", "second position providing unit") and/or "controller" may be hardware and/or software-based components. In particular these units and/or controller may be found as codes of computer program, or instructions, stored in a non-transitory memory, and arranged to be executed by a processor causing the control device to implement the control according to the different embodiments of the invention.

The control device may be a computer system or computer device or computer unit including at least one memory, where, if a plurality of memories, memories in the computer system communicate with each other and the processor via a bus. Either or a plurality of said memories may be considered representative examples of "the" memory of the control device, and store instructions used to implement some or all aspects of methods and processes described herein. Memory(ies) described herein and according to the invention is (are) tangible storage medium(s) for storing data and executable software instructions and is (are) non-transitory during the time software instructions are stored therein. As used herein, the term “non-transitory” is to be interpreted not as an eternal characteristic of a state, but as a characteristic of a state that will last for a period. The term “non-transitory” specifically disavows fleeting characteristics such as characteristics of a carrier wave or signal or other forms that exist only transitorily in any place at any time. Memory(ies) is (are) article(s) of manufacture and/or machine components. It (they) is (are) computer-readable medium(s) from which data and executable software instructions can be read by a computer (or a processor). Memory(ies) may be implemented as one or more of random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, Blu-ray disk, or any other form of storage medium known in the art. The memories may be volatile or non-volatile, secure and/or encrypted, unsecure and/or unencrypted.

“Memory” is an example of a computer-readable storage medium. Computer memory is any memory which is directly accessible to a processor. Examples of computer memory include, but are not limited to RAM memory, registers, and register files. References to “computer memory” or “memory” should be interpreted as possibly being multiple memories. The memory may for instance be multiple memories within the same computer system. The memory may also be multiple memories distributed amongst multiple computer systems or computing devices.

The computer system or device or unit may further include a video display unit, such as a liquid crystal display (LCD), an organic light emitting diode (OLED), a flat panel display, a solid-state display, or a cathode ray tube (CRT), for example. Additionally, the computer system or device or unit may include an input device, such as a keyboard/virtual keyboard or touch-sensitive input screen or speech input with speech recognition, and a cursor control device, such as a mouse or touch-sensitive input screen or pad. The computer system or device or unit also optionally includes a disk drive unit, a signal generation device, such as a speaker or remote control, and/or a network interface device.

The disk drive unit may include a computer-readable medium in which one or more sets of software instructions (software) are embedded. The sets of software instructions are read from the computer-readable medium to be executed by the processor. Further, the software instructions, when executed by the processor, perform one or more steps of the methods and processes as described herein. In an embodiment, the software instructions reside all or in part within a memory (e.g. a main or static memory) and/or the processor during execution by the computer system or device or unit. Further, the computer-readable medium may include software instructions or receive and execute software instructions responsive to a propagated signal, so that a device connected to a network communicates voice, video or data over the network. The software instructions may be transmitted or received over the network via the network interface device.

In an embodiment, dedicated hardware implementations, such as application-specific integrated circuits (ASICs), field programmable gate arrays (FPGAs), programmable logic arrays and other hardware components, are constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing may implement one or more of the methods or functionalities as described herein, and a processor described herein may be used to support a virtual processing environment.

The invention claimed is:

1. A system comprising:

a first instrument;

a second instrument configured to induce a motion upon the first instrument; and a processor that executes instructions for controlling a movement of the first instrument and the second instrument along a tubular anatomical structure, wherein, when executed by the processor, the instructions cause the processor to:

provide an indicator of a limiting position for an instrument beyond which position of the first instrument is considered as out-of-limit;

provide the position of the first instrument from an image including at least one of a portion of the first instrument and retrieved movement of the first instrument, wherein the image includes a portion of the first instrument and the second instrument and a branched intersection of a plurality of branches of the tubular anatomical structure including a main branch and a target branch which is branched from the main branch;

maintain the first instrument at a target point in a target branch of the tubular anatomical structure; and control a movement of the first instrument based on the indicator of the limiting position and the position of the first instrument such that the position of the first instrument maintains a predetermined relation with respect to the limiting position, wherein the movement of the first instrument is of an amount compensating for a retraction of the second instrument.

2. The system of claim 1, wherein the instructions further cause the processor to provide a representation of the indicator in the image so as to graphically represent the limiting position.

3. The system as defined in claim 2, wherein the instrument is a medical instrument, and wherein the instructions further cause the processor to control a movement of the instrument along a tubular anatomical structure, wherein a portion of the tubular anatomical structure is included in the image, and wherein the representation of the indicator is provided across an imaged tubular structure.

4. The system as defined in claim 3, wherein the instructions further cause the processor to provide the representation of the indicator with a size that is provided across an imaged tubular structure and dynamically changes with a potential change of width of the imaged tubular structure.

5. The system of claim 1, wherein the second instrument is manually driven and is configured to induce a motion upon the first instrument, wherein the instructions further cause the processor to control the first instrument so as to automatically maintain the predetermined relation with respect to the limiting position while the second instrument is manually driven.

6. The system of claim 1, wherein the instructions further cause the processor to:

provide a target indicator indicative of a target position for the second instrument to be moved, and provide a second position that comprises a position of the second instrument.

7. The system of claim 6, wherein the instructions further cause the processor to at least one of:

control a movement of the second instrument based on the target indicator and the second position such that the second position approaches the target position;

trigger an alert for a user when the second instrument approaches the target position beyond an alert limit;

control a movement of the second instrument based on the target indicator and the second position such that the movement of the second instrument slows down when the second position is beyond an approach limit, and control a counteracting force applied to the second instrument or to a tool driving the second instrument, the counteracting force being opposite to a manual force exerted by the user who would manually drive the second instrument, the counteracting force being exerted when the second position is beyond an approach limit, wherein the approach limit is the target position and the counteracting force is sufficiently high to prevent the user to manually drive the second instrument beyond the target position, wherein the counteracting force gradually increases between the approach limit and the target position.

8. The system of claim 1, wherein the first instrument and the second instrument are medical instruments, wherein the instructions further cause the processor to control a movement of the first instrument and the second instrument along a tubular anatomical structure.

9. The system of claim 1, wherein the instructions further cause the processor to determine a distance between the position of the first instrument for which the indicator of the limiting position is provided and the limiting position, and to control the movement of the first instrument based on the distance.

10. The system of claim 9, wherein the position of the first instrument for which the indicator of the limiting position is provided from the received image of a portion of the first instrument, wherein the limiting position refers to a position in the image, and wherein the distance is determined based on the image.

11. The system of claim 1, wherein the instructions further cause the processor to provide the indicator for the limiting position based on an imaged anatomical feature comprising a new branch where the first instrument enters into, if the first instrument is moved at least one of along a tubular anatomical structure, and on a user input through a user interface configured to associate a user input with at least one of a location in the image and on stored predefined setting parameters.

12. The system of claim 11, wherein the instructions further cause the processor to provide the indicator of the limiting position based further on the position of the first instrument.

13. The system of claim 1, wherein the instructions further cause the processor to detect when the position of the first instrument to be moved does not change although the first instrument is controlled to move beyond a threshold distance, and to modify the movement of the first instrument or to trigger an alert to a user.

14. An apparatus for moving a medical instrument, the apparatus comprising:

the system of claim 1, a drive controllable by the processor of the control device to drive the movement of the first instrument to be moved.

15. The apparatus as defined in claim 14, further comprising the first instrument and the second instrument, wherein at least one of:

a) the first instrument refers to a flexible elongate guiding instrument and the second instrument refers to an instrument to be guided along the first instrument, and b) the second instrument refers to a flexible elongate guiding instrument and the first instrument refers to an instrument to be guided along the first instrument.

16. A method for controlling movement of a medical instrument, the method comprising:

providing an indicator of a limiting position for a first instrument beyond which position of the first instrument is considered as out-of-limit;

providing the position of the first instrument from an image including at least one of a portion of the first instrument and retrieved movement of the first instrument, wherein the image includes a portion of the first instrument and a second instrument and a branched intersection of a plurality of branches of a tubular anatomical structure including a main branch and a target branch which is branched from the main branch;

maintaining the first instrument at a target point in a target branch of the tubular anatomical structure and controlling a movement of the first instrument based on the indicator of the limiting position and the position of the first instrument such that the position of the first instrument maintains a predetermined relation with respect to the limiting position, wherein the movement of the instrument is of an amount compensating for a retraction of the second instrument.

17. A non-transitory computer-readable medium having stored a computer program which comprises instructions which, when executed by a processor, causes the processor to:

provide an indicator of a limiting position for a first instrument beyond which position of the first instrument is considered as out-of-limit;

provide the position of the first instrument from an image including at least one of a portion of the first instrument and retrieved movement of the first instrument, wherein the image includes a portion of the first instrument and a second instrument and a branched intersection of a plurality of branches of a tubular anatomical structure including a main branch and a target branch which is branched from the main branch;

maintain the first instrument at a target point in a target branch of the tubular anatomical structure; and control a movement of the first instrument based on the indicator of the limiting position and the position of the first instrument such that the position of the first instrument maintains a predetermined relation with respect to the limiting position, wherein the movement of the first instrument is of an amount compensating for a retraction of the second instrument.

* * * * *